(12) United States Patent
Pontoppidan

(10) Patent No.: US 7,979,888 B2
(45) Date of Patent: Jul. 12, 2011

(54) PRIVACY MARKUP ON ENTITY MODELS

(75) Inventor: Michael Fruergaard Pontoppidan, Lynge (DK)

(73) Assignee: Microsoft Corporation, Redmond, WA (US)

( * ) Notice: Subject to any disclaimer, the term of this patent is extended or adjusted under 35 U.S.C. 154(b) by 1290 days.

(21) Appl. No.: 10/992,960

(22) Filed: Nov. 19, 2004

(65) Prior Publication Data

US 2006/0129507 A1  Jun. 15, 2006

(51) Int. Cl.
*G06F 7/00* (2006.01)
*G06Q 50/00* (2006.01)

(52) U.S. Cl. .......... 726/1; 726/26; 705/1.1; 705/2; 705/3

(58) Field of Classification Search .......... 726/1, 26; 705/1.1, 2, 3
See application file for complete search history.

(56) References Cited

U.S. PATENT DOCUMENTS

| | | | |
|---|---|---|---|
| 6,438,544 B1* | 8/2002 | Grimmer et al. | 707/5 |
| 7,225,460 B2* | 5/2007 | Barzilai et al. | 726/1 |
| 7,266,846 B2* | 9/2007 | King et al. | 726/26 |
| 7,269,578 B2* | 9/2007 | Sweeney | 705/74 |
| 2003/0061073 A1* | 3/2003 | Seow et al. | 705/3 |
| 2006/0046742 A1* | 3/2006 | Zhang | 455/456.2 |

OTHER PUBLICATIONS

Inherit, Inheritance, Inheritance Code. In Microsoft Computer Dictionary. Microsoft Press 2002.*

* cited by examiner

*Primary Examiner* — Kambiz Zand
*Assistant Examiner* — Imhotep Durham
(74) *Attorney, Agent, or Firm* — Turk IP Law, LLC

(57) ABSTRACT

A method of identifying an entry in an entity model as being at least one of potentially private and potentially sensitive is disclosed. The method may include creating an indication related to a specific entry that indicates whether the specific entry is one of potentially personally identifiable and potentially sensitive or both and allowing the indication to be modified to indicate whether the specific entry is one of potentially personally identifiable and potentially sensitive or both.

18 Claims, 5 Drawing Sheets

PRIVACY MARKUP ON ENTITY MODELS

BACKGROUND

Privacy of personal data in computer systems is rapidly growing in importance. As identity theft has increased, the need to protect data has increased. Also, the sophistication of identity thieves has increased exponentially, resulting in increasingly aggressive attempts to obtain personal or sensitive information. At the same time, more and more information is being stored in a digital manner. Further, users inputting data may not even realize that data being entered would be sensitive or personally identifiable, especially when the entered data is combined with additional data.

SUMMARY

A method of identifying an entry in an entity model as being at least one of potentially private and potentially sensitive is disclosed. The method may include creating an indication related to a specific entry that indicates whether the specific entry is one of potentially personally identifiable and potentially sensitive and allowing the indication to be modified to indicate whether the specific entry is one of potentially personally identifiable and potentially sensitive or both.

The specific entry alone may not be at least one of personally identifiable and potentially sensitive but would be one of potentially personally identifiable and potentially sensitive when combined with additional data. The indication may indicate whether the specific entry is potentially personally identifiable alone or is potentially identifiable when combined with additional data. The method may be applied to a relational database, an XML schema or an object model. The indication may be a boolean entry and the default value of the indication may be that the entry is one of potentially personally identifiable and potentially sensitive.

The entity model may have at least one entity and each entity may have at least one property and each property may have at least one attribute and an attribute may be used to indicate whether the property is at least one of potentially personally identifiable entry and potentially sensitive entry or the entity model may have at least one entity and each entity may have at least one property and where each property is a specialization of one data type and where each data type may have at least one attribute that indicates whether the data type contains at least one of potentially personally identifiable entry and potentially sensitive entry. A first attribute may indicate whether an entry is a potentially personally identifiable entry and a second attribute may indicate whether an entry is a potentially sensitive entry. The method may be used in connection with a customer relation management system. A memory that is programmed to execute the method and a system program to execute the method also are disclosed.

DRAWINGS

DESCRIPTION

Although the following text sets forth a detailed description of numerous different embodiments, it should be understood that the legal scope of the description is defined by the words of the claims set forth at the end of this patent. The detailed description is to be construed as exemplary only and does not describe every possible embodiment since describing every possible embodiment would be impractical, if not impossible. Numerous alternative embodiments could be implemented, using either current technology or technology developed after the filing date of this patent, which would still fall within the scope of the claims.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term by limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

Figure 1:
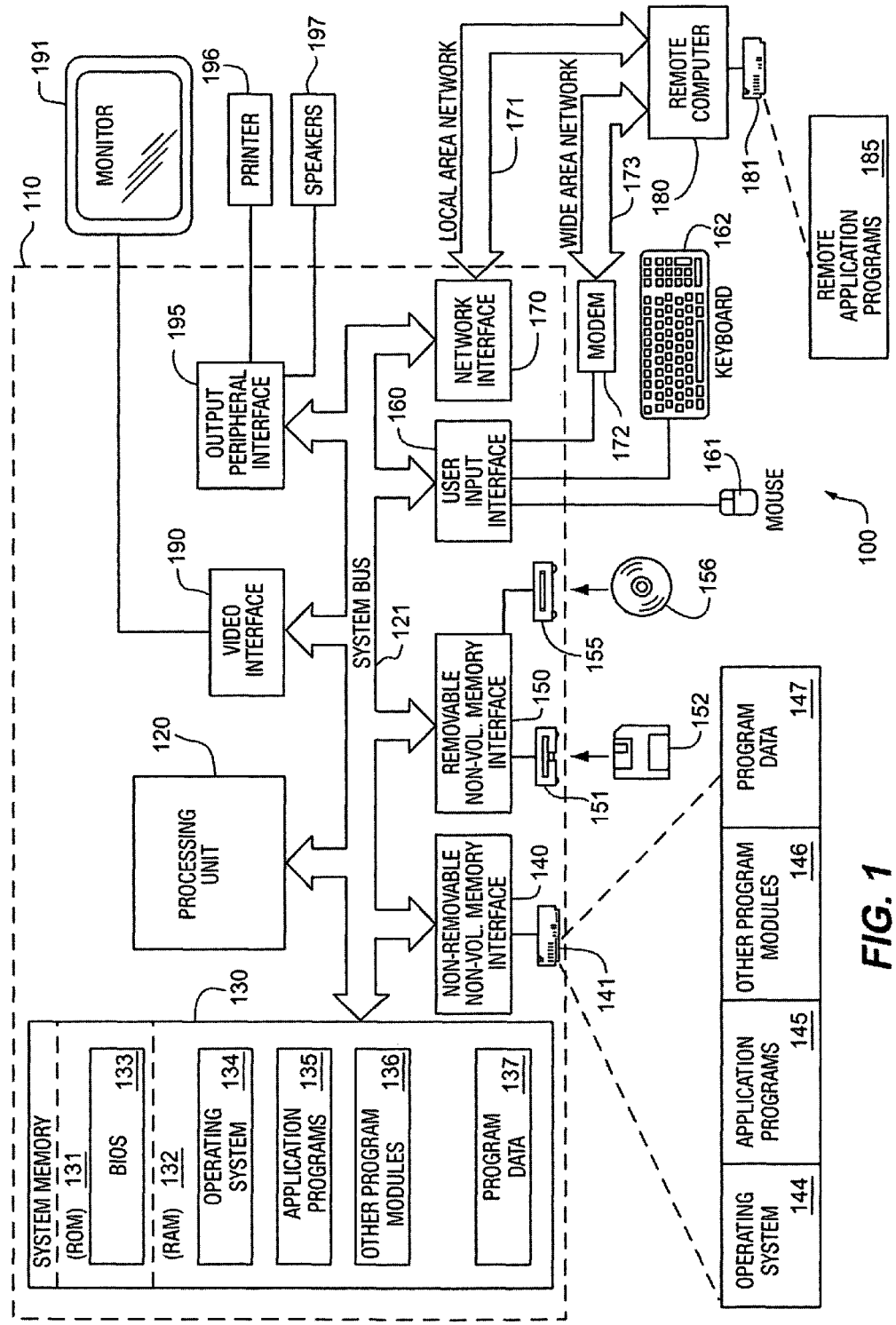
FIG. 1 is a block diagram of a computing system that may operate in accordance with the claims.

FIG. 1 illustrates an example of a suitable computing system environment 100 on which a system for the steps of the claimed method and apparatus may be implemented. The computing system environment 100 is only one example of a suitable computing environment and is not intended to suggest any limitation as to the scope of use or functionality of the method of apparatus of the claims. Neither should the computing environment 100 be interpreted as having any dependency or requirement relating to any one or combination of components illustrated in the exemplary operating environment 100.

The steps of the claimed method and apparatus are operational with numerous other general purpose or special purpose computing system environments or configurations. Examples of well known computing systems, environments, and/or configurations that may be suitable for use with the methods or apparatus of the claims include, but are not limited to, personal computers, server computers, hand-held or laptop devices, multiprocessor systems, microprocessor-based systems, set top boxes, programmable consumer electronics, network PCs, minicomputers, mainframe computers, distributed computing environments that include any of the above systems or devices, and the like.

The steps of the claimed method and apparatus may be described in the general context of computer-executable instructions, such as program modules, being executed by a computer. Generally, program modules include routines, programs, objects, components, data structures, etc. that perform particular tasks or implement particular abstract data types. The methods and apparatus may also be practiced in distributed computing environments where tasks are performed by remote processing devices that are linked through a communications network. In a distributed computing environment, program modules may be located in both local and remote computer storage media including memory storage devices.

With reference to FIG. 1, an exemplary system for implementing the steps of the claimed method and apparatus includes a general purpose computing device in the form of a computer 110. Components of computer 110 may include, but are not limited to, a processing unit 120, a system memory 130, and a system bus 121 that couples various system components including the system memory to the processing unit 120. The system bus 121 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

Computer 110 typically includes a variety of computer readable media. Computer readable media can be any available media that can be accessed by computer 110 and includes both volatile and nonvolatile media, removable and non-removable media. By way of example, and not limitation, computer readable media may comprise computer storage media and communication media. Computer storage media includes both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can accessed by computer 110. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media.

The system memory 130 includes computer storage media in the form of volatile and/or nonvolatile memory such as read only memory (ROM) 131 and random access memory (RAM) 132. A basic input/output system 133 (BIOS), containing the basic routines that help to transfer information between elements within computer 110, such as during start-up, is typically stored in ROM 131. RAM 132 typically contains data and/or program modules that are immediately accessible to and/or presently being operated on by processing unit 120. By way of example, and not limitation, FIG. 1 illustrates operating system 134, application programs 135, other program modules 136, and program data 137.

The computer 110 may also include other removable/non-removable, volatile/nonvolatile computer storage media. By way of example only, FIG. 1 illustrates a hard disk drive 140 that reads from or writes to non-removable, nonvolatile magnetic media, a magnetic disk drive 151 that reads from or writes to a removable, nonvolatile magnetic disk 152, and an optical disk drive 155 that reads from or writes to a removable, nonvolatile optical disk 156 such as a CD ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 141 is typically connected to the system bus 121 through a non-removable memory interface such as interface 140, and magnetic disk drive 151 and optical disk drive 155 are typically connected to the system bus 121 by a removable memory interface, such as interface 150.

The drives and their associated computer storage media discussed above and illustrated in FIG. 1, provide storage of computer readable instructions, data structures, program modules and other data for the computer 110. In FIG. 1, for example, hard disk drive 141 is illustrated as storing operating system 144, application programs 145, other program modules 146, and program data 147. Note that these components can either be the same as or different from operating system 134, application programs 135, other program modules 136, and program data 137. Operating system 144, application programs 145, other program modules 146, and program data 147 are given different numbers here to illustrate that, at a minimum, they are different copies. A user may enter commands and information into the computer 20 through input devices such as a keyboard 162 and pointing device 161, commonly referred to as a mouse, trackball or touch pad. Other input devices (not shown) may include a microphone, joystick, game pad, satellite dish, scanner, or the like. These and other input devices are often connected to the processing unit 120 through a user input interface 160 that is coupled to the system bus, but may be connected by other interface and bus structures, such as a parallel port, game port or a universal serial bus (USB). A monitor 191 or other type of display device is also connected to the system bus 121 via an interface, such as a video interface 190. In addition to the monitor, computers may also include other peripheral output devices such as speakers 197 and printer 196, which may be connected through an output peripheral interface 190.

The computer 110 may operate in a networked environment using logical connections to one or more remote computers, such as a remote computer 180. The remote computer 180 may be a personal computer, a server, a router, a network PC, a peer device or other common network node, and typically includes many or all of the elements described above relative to the computer 110, although only a memory storage device 181 has been illustrated in FIG. 1. The logical connections depicted in FIG. 1 include a local area network (LAN) 171 and a wide area network (WAN) 173, but may also include other networks. Such networking environments are commonplace in offices, enterprise-wide computer networks, intranets and the Internet.

When used in a LAN networking environment, the computer 110 is connected to the LAN 171 through a network interface or adapter 170. When used in a WAN networking environment, the computer 110 typically includes a modem 172 or other means for establishing communications over the WAN 173, such as the Internet. The modem 172, which may be internal or external, may be connected to the system bus 121 via the user input interface 160, or other appropriate mechanism. In a networked environment, program modules depicted relative to the computer 110, or portions thereof, may be stored in the remote memory storage device. By way of example, and not limitation, FIG. 1 illustrates remote application programs 185 as residing on memory device 181. It will be appreciated that the network connections shown are exemplary and other means of establishing a communications link between the computers may be used.

Figure 2:
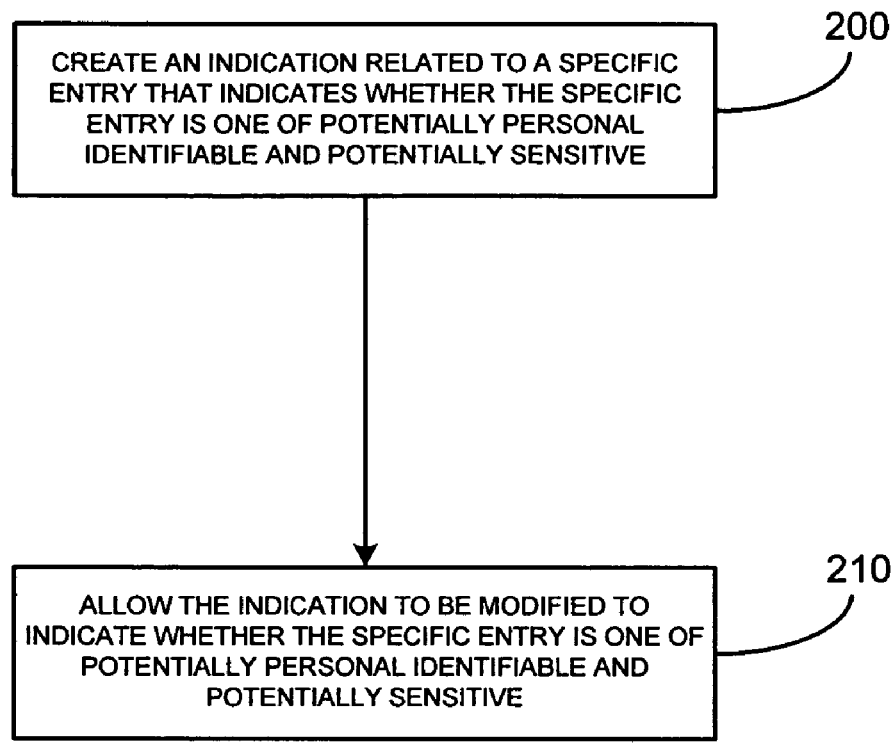
FIG. 2 is a flowchart of an embodiment in accordance with the claims.

FIG. 2 illustrates a method of identifying an entry in an entity model as being at least one of potentially private and potentially sensitive in accordance with the claims. At block 200, an indication related to a specific entry that indicates whether the specific entry is one of potentially personally identifiable and potentially sensitive is created. At block 210, the indication may be modified by a user with permission to indicate whether the specific entry is one of potentially personally identifiable and potentially sensitive.

Figure 3:
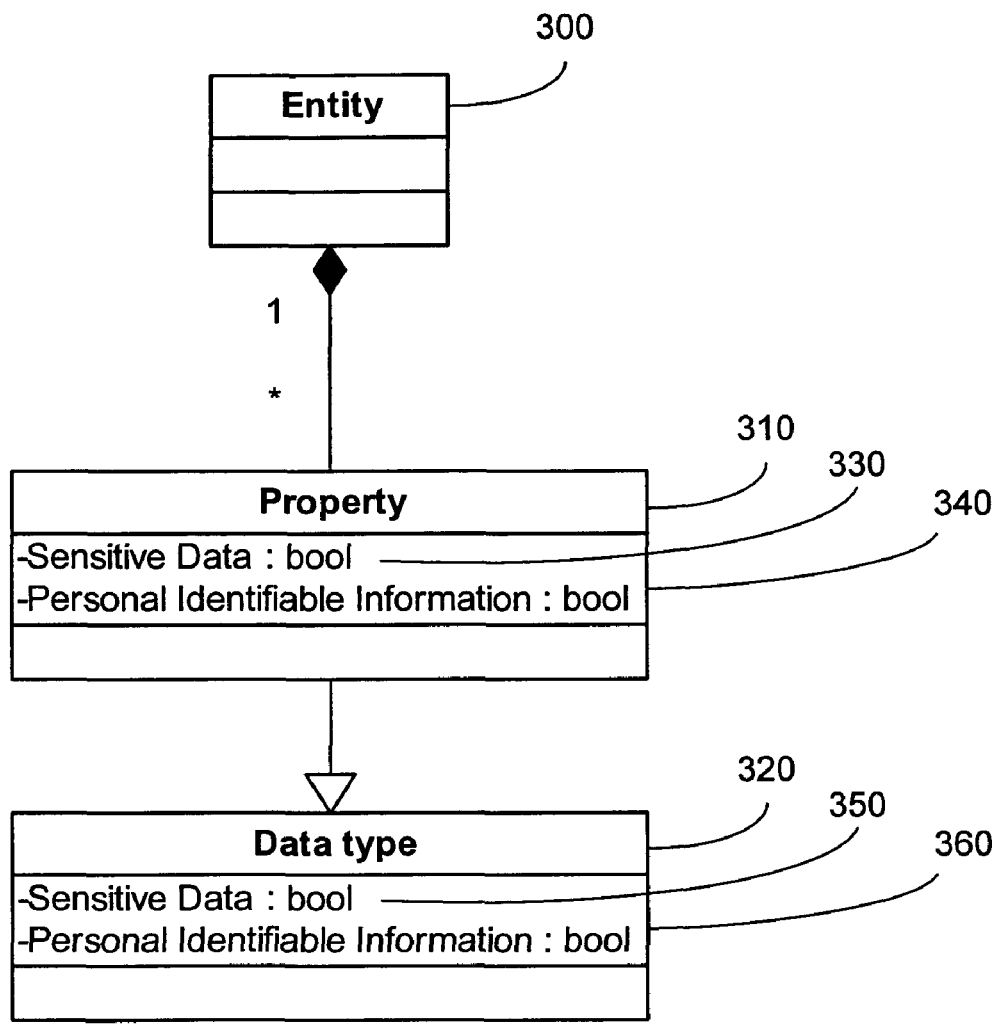
FIG. 3 is an illustration of an entity model in accordance with the claims.

FIG. 3 illustrates an entity model. An entity model may consist of at least one entity; and an entity is composed of at least one property. In modern entity models each property may be a specialization of one data type. To get the full benefit of the claimed method and apparatus, data types may be used but data types are not necessary.

For example, an entity could be an "employee" 300 and an "employee" 300 has several properties, one of them being "home phone number" 310, which is a specialization of the data type "phone number" 320. In one example, two boolean (Yes/No) attributes may be added to each property 330, 340 and each data type 350, 360. As a property is a specialization of a data type, it may inherit the privacy attribute values from the data type. These values may be overridden.

In one example, a customer relationship management ("CRM") system allows for the input of data in numerous attributes where the attributes hold data that may be of benefit to the user of the system. Say a law firm is using the CRM system. Members of the law firm could input names, phone numbers and corporate affiliations of potential contacts. The CRM system may be of use to the entire firm such that when a user searches for contacts at a certain corporation (say Microsoft) all the entries in the CRM system that are related to Microsoft may be displayed. However, certain people inside the law firm may know the workers at Microsoft quite well and may input information into the CRM system that could be considered sensitive, such as home addresses, home telephone numbers, private email addresses, names of children, etc. This information may be available to everyone in the law firm using the CRM system. While someone close to the contact would be trusted with the personal or sensitive information, that trust does not automatically extend to everyone in the law firm.

Accordingly, it may be useful have the ability to mark every attribute to be sensitive information or personally identifiable information. It also may be useful to have default values of whether certain known attributes are sensitive information or personally identifiable information. It may also be desirable to only allow a user with permission be allowed to modify the indication such as a developer or someone with developer privileges.

What is sensitive information may vary on a case-by-case basis, but some default rules may be created that would classify some information as being sensitive. As an example, some people may consider attributes such as their home address, home phone number, home email address and names of children to be sensitive information. The loss of sensitive information may not necessarily result in identity theft, for example, but nonetheless is information that people would appreciate being kept out of the public domain.

Figure 4:
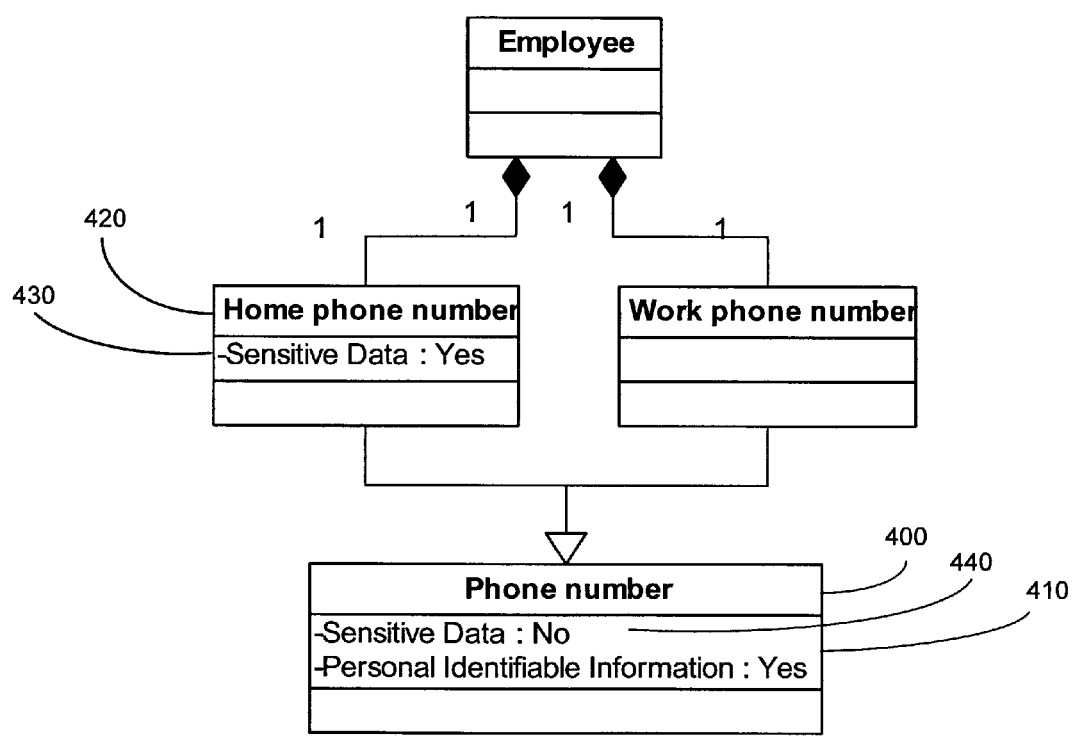
FIG. 4 is an illustration of an entity model in accordance with the claims.

FIG. 4 illustrates a further example. A data type might not make the data sensitive in it self, but used in a given context, it might. For example, properties based on the data type phone number 400 are not necessarily sensitive data 410. When the property holds an employee's home phone number 420, it may be sensitive information 430.

As another example, the fact that a person has a spouse may not be sensitive. However, the fact that a person has multiple spouses at the same time may be sensitive information. By combining multiple attributes, sensitive information may be obtained. For example, combining the fact that a person has a spouse with the fact that the same person has an additional spouse may result in all the spousal information being sensitive. As another example, obtaining the expiration date of a credit card may not be sensitive. However, combining the expiration date of the credit card with the actual credit card number may result in the creation of sensitive information. Such data, while not sensitive alone, could be sensitive when combined with additional data, and as such, may be indicated in the system.

Personally identifiable information is information that may be used to identify a person. In the United States, a social security number or passport number would be personally identifiable information. Similar identification numbers may exist in different countries around the world. In addition, a credit card number may be personally identifiable information. There may be variety of reasons to indicate personally identifiable information with identity theft being the most obvious.

Figure 5:
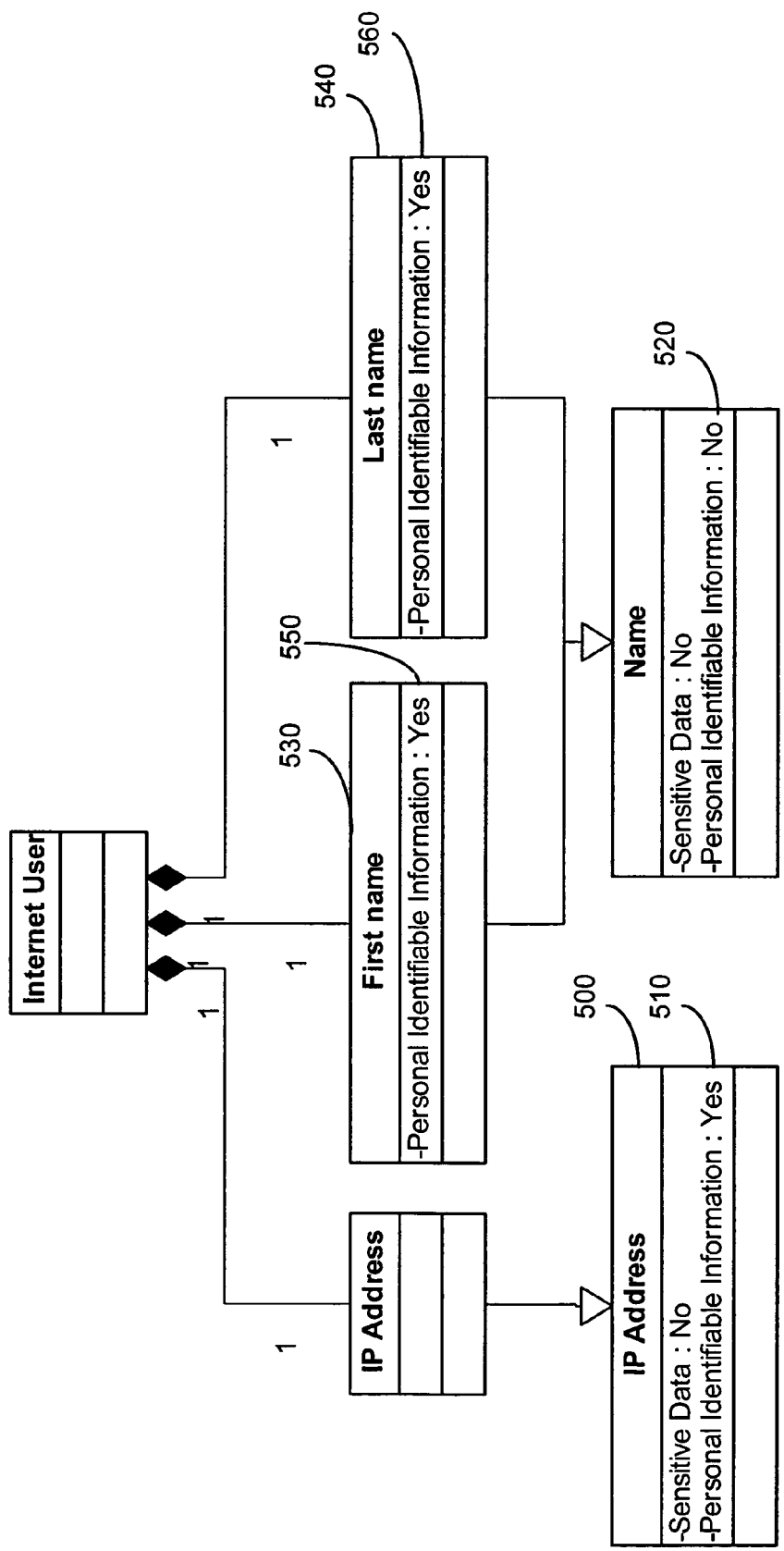
FIG. 5 is an illustration of an entity model in accordance with the claims.

Combinations of information may also result in the creation of personally identifiable information. Some information may not be personally identifiable information until it is combined with other information. FIG. 5 illustrates one example. An IP-Address 500 may be personally identifiable information in itself 510, whereas a generic name is not personally sensitive information 520, but combining a person's first name 530 with a last name 540 and perhaps also a company, address or just city may result in personally identifiable information 550, 560.

Some information may be sensitive data and not personally identifiable information and vice versa. Referring again to FIG. 4, a phone number 400 may not be sensitive data 410 but it may be personally identifiable information 440.

The manner in which the indication of an attribute being personally sensitive information or personally identifiable can be varied. For example, a simple boolean entry may be the indication. In another example, a single entry may be used to indicate both whether an attribute is personally sensitive information and personally identifiable. For example, a first digit may mean an attribute is personally sensitive information and a second digit may indicate an attribute is personally identifiable. Even less complex codes are possible, such as 0 may mean the attribute is neither personally sensitive information or personally identifiable, 1 may mean the attribute is personally sensitive information but not personally identifiable, 2 may mean the attribute is personally identifiable but not personally sensitive information and 3 may mean the attribute is both personally sensitive information and personally identifiable. In addition, codes may be used in conjunction with a lookup table to convert the code to have meaning. Obviously, numerous other indications are possible and acceptable.

Not just anyone may be permitted to modify the indication of whether an attribute is personally sensitive information or personally identifiable. Permission may be required to modify the indication or else an undesirable user could be permitted to change the indication.

The method may applicable to numerous instances. Obvious examples include a relational database, an XML schema, and virtually any object model such as a CRM system. As just an example, using a CRM system, a disgruntled employee could attempt to obtain a home phone number of a valued client. If the home phone number is indicated as being personally identifiable information or personally sensitive information, access to the home phone number may be denied. In addition, the default value for "home address" may be marked as personally sensitive information or personally identifiable so when information is inputted into the CRM system, the person inputting the information does not have to make difficult choices of whether data is personally sensitive information or personally identifiable as this information may be set up during the initial program installation or by the software manufacturer itself.

Although the forgoing text sets forth a detailed description of numerous different embodiments, it should be understood that the scope of the patent is defined by the words of the claims set forth at the end of this patent. The detailed description is to be construed as exemplary only and does not describe every possible embodiment because describing every possible embodiment would be impractical, if not impossible. Numerous alternative embodiments could be implemented, using either current technology or technology developed after the filing date of this patent, which would still fall within the scope of the claims.

Thus, many modifications and variations may be made in the techniques and structures described and illustrated herein without departing from the spirit and scope of the present claims. Accordingly, it should be understood that the methods and apparatus described herein are illustrative only and are not limiting upon the scope of the claims.

The invention claimed is:

1. A computer that is physically configured to implement a method of identifying an entry in an entity model as being at least one of potentially private and potentially sensitive if the entry is combined with one or more specified entries wherein the method comprises:
   creating an indication related to a specific entry in the entity model wherein the entity model has at least one entity and
   each entity has at least one property and
      where each property is a specialization of one data type and
         where each data type has at least one attribute that indicates whether the data type contains at least one of potentially personally identifiable entry and potentially sensitive entry if the entry is combined with one or more specified entries and
   wherein the entity model is a relational database that indicates whether the specific entry is one of potentially personally identifiable and potentially sensitive wherein
   a first attribute indicates whether an entry is a potentially personally identifiable entry if the entry is combined with one or more specified entries or with a data type wherein the potentially identifiable entry comprises information that may be used to identify a specific person;
   a second attribute indicates whether an entry is a potentially sensitive entry if the entry is combined with one or more specified entries or with a data type wherein the potentially sensitive entry comprises information that is desired to be kept from the public; and
   a default value of the indication is that the entry is one of:
      potentially personally identifiable if the entry is combined with one or more specified entries or with a data type,
      potentially sensitive if the entry is combined with one or more specified entries or with a data type;
      personally identifiable and potentially sensitive;
      the specific entry alone is not at least one of personally identifiable and potentially sensitive
      but would be one of
         potentially personally identifiable and potentially sensitive
         when combined with one or more additional specified entries or with a data type; and
      allowing the indication to be modified by a user with permission to indicate whether the specific entry is one of potentially personally identifiable and potentially sensitive
         if the entry is combined with one or more specified entries or with a data type.

2. The computer of claim 1, wherein the indication indicates whether the specific entry is potentially personally identifiable alone or is potentially identifiable when combined with additional data.

3. The computer of claim 1, wherein the entity model is an XML schema.

4. The computer of claim 1, wherein the entity model is an object model.

5. The computer of claim 1, wherein the entity model has at least one entity and each entity has at least one property and each property has at least one attribute and an attribute is used to indicate whether the property is at least one of potentially personally identifiable entry and potentially sensitive entry if the entry is combined with one or more specified entries.

6. The computer of claim 1, wherein the method is used in connection with a customer relation management system.

7. A computer readable medium having computer executable instructions for identifying an entry in an entity model as being at least one of potentially private and potentially sensitive if the entry is combined with one or more specified entries, the instructions comprising:
   creating an indication related to a specific entry in the entity model wherein the entity model has at least one entity and
   each entity has at least one property and
      where each property is a specialization of one data type and
         where each data type has at least one attribute that indicates whether the data type contains at least one of potentially personally identifiable entry and potentially sensitive entry if the entry is combined with one or more specified entries and
   wherein the entity model is a relational database that indicates whether the specific entry is one of potentially personally identifiable and potentially sensitive if the entry is combined with one or more specified entries or with a data type wherein
   a first attribute indicates whether an entry is a potentially personally identifiable entry if the entry is combined with one or more specified entries or with a data type wherein the potentially identifiable entry comprises information that may be used to identify a specific person; and
   a second attribute indicates whether an entry is a potentially sensitive entry if the entry is combined with one or more specified entries or with a data type wherein the potentially sensitive entry comprises information that is desired to be kept from the public; and
   a default value of the indication is that the entry is one of:
      potentially personally identifiable,
      potentially sensitive
      personally identifiable and potentially sensitive;
      the specific entry alone is not at least one of personally identifiable and potentially sensitive but would be one of
   potentially personally identifiable and
   potentially sensitive when combined with additional
      if the entry is combined with one or more specified entries or with a data type; and
   allowing the indication to be modified by a user with permission to indicate whether the specific entry is one of
      potentially personally identifiable and
      potentially sensitive
      if the entry is combined with one or more specified entries or with a data type.

8. The computer readable medium of claim 7, wherein the indication indicates whether the specific entry is potentially personally identifiable alone or is potentially identifiable if the entry is combined with one or more specified entries or with a data type.

9. The computer readable medium of claim 7, wherein the entity model is an XML schema.

10. The computer readable medium of claim 7, wherein the entity model is an object model.

11. The computer readable medium of claim 7, wherein the entity model has at least one entity and each entity has at least one property and each property has at least one attribute and an attribute is used to indicate whether the property is at least one of potentially personally identifiable entry and potentially sensitive entry.

12. The computer readable medium of claim 7, wherein the steps is used in connection with a customer relation management system.

13. A computing apparatus, comprising:
   a display unit that is capable of generating video images;
   an input device;
   a processing apparatus operatively coupled to said display unit and said input device, said processing apparatus comprising a processor and a memory operatively coupled to said processor,
   a network interface connected to a network and to the processing apparatus;
said processing apparatus being programmed to
   create an indication related to a specific entry in the entity model wherein the entity model has at least one entity and
      each entity has at least one property and
         where each property is a specialization of one data type and
            where each data type has at least one attribute that indicates whether the data type contains at least one of potentially personally identifiable entry and potentially sensitive entry if the entry is combined with one or more specified entries; and
   wherein the entity model is a relational database that indicates whether the specific entry is one of
      potentially personally identifiable and
      potentially sensitive wherein
         a first attribute indicates whether an entry is a potentially personally identifiable entry if the entry is combined with one or more specified entries or with a data type wherein the potentially identifiable entry comprises information that may be used to identify a specific person and
         a second attribute indicates whether an entry is a potentially sensitive entry if the entry is combined with one or more specified entries or with a data type wherein the potentially sensitive entry comprises information that is desired to be kept from the public and
      a default value of the indication is that the entry is one of
         potentially personally identifiable,
         potentially sensitive
         personally identifiable and
         potentially sensitive;
   the specific entry alone is not at least one of
      personally identifiable and
      potentially sensitive
   but would be one of
      potentially personally identifiable and
      potentially sensitive if the entry is combined with one or more specified entries or with a data type; and
   allow the indication to be modified by a user with permission to indicate whether the specific entry is one of
      potentially personally identifiable and
      potentially sensitive if the entry is combined with one or more specified entries or with a data type.

14. The computing apparatus of claim 13, wherein the indication indicates whether the specific entry is potentially personally identifiable alone or is potentially identifiable if the entry is combined with one or more specified entries or with a data type.

15. The computing apparatus of claim 13, wherein the entity model is an XML schema.

16. The computing apparatus of claim 13, wherein the entity model is an object model.

17. The computing apparatus of claim 13, wherein the entity model has at least one entity and each entity has at least one property and each property has at least one attribute and an attribute is used to indicate whether the property is at least one of potentially personally identifiable entry and potentially sensitive entry if the entry is combined with one or more specified entries or with a data type.

18. The computing apparatus of claim 13, wherein the processing apparatus is used in connection with a customer relation management system.

* * * * *